(12) United States Patent
Everett (10) Patent No.: US 10,436,774 B1
(45) Date of Patent: Oct. 8, 2019

(54) GLOVE HAVING CHROMOGENIC MATERIAL

(71) Applicant: Cathy Everett, Park Forest, IL (US)

(72) Inventor: Cathy Everett, Park Forest, IL (US)

(*) Notice: Subject to any disclaimer, the term of this patent is extended or adjusted under 35 U.S.C. 154(b) by 245 days.

(21) Appl. No.: 15/596,119

(22) Filed: May 16, 2017

(51) Int. Cl.
*A41D 19/00* (2006.01)
*G01N 33/52* (2006.01)
*A61B 42/10* (2016.01)

(52) U.S. Cl.
CPC ....... *G01N 33/528* (2013.01); *A41D 19/0075* (2013.01); *A61B 42/10* (2016.02)

(58) Field of Classification Search
CPC ... A61B 5/6806; A61B 10/0038; A61B 42/00; A61B 42/10; A61B 5/411; A41D 19/0062; A41D 19/0075
USPC .......................................................... 2/161.7
See application file for complete search history.

(56) References Cited

U.S. PATENT DOCUMENTS

| | | | | |
|---|---|---|---|---|
| 3,672,351 A * | 6/1972 | Ubersax | ................. | A61B 42/10 422/411 |
| 4,231,370 A | 11/1980 | Mroz | | |
| 5,650,329 A * | 7/1997 | Warner | ................. | G01N 31/221 422/414 |
| 5,947,943 A | 9/1999 | Lee | | |
| 6,075,178 A | 6/2000 | Wilhelm | | |
| D589,666 S | 3/2009 | Crater | | |
| 7,725,957 B2 | 6/2010 | Arai | | |
| 7,938,776 B2 * | 5/2011 | Barnes, Sr. | ............ | A61B 5/411 422/418 |
| 8,985,469 B2 * | 3/2015 | Coombes | ........... | A41D 19/0062 235/375 |
| 9,018,435 B2 | 4/2015 | Kawashima | | |
| 2006/0140994 A1 * | 6/2006 | Bagwell | ...................... | C08J 5/02 424/404 |
| 2008/0108965 A1 | 5/2008 | Christensen | | |
| 2010/0111763 A1 * | 5/2010 | Kahn | ................. | A61B 5/02042 422/400 |
| 2011/0034896 A1 | 2/2011 | Bai | | |
| 2016/0325075 A1 * | 11/2016 | Madigan | ........... | A61M 25/0017 |
| 2018/0332910 A1 * | 11/2018 | Modha | ............... | A41D 19/0006 |

FOREIGN PATENT DOCUMENTS

WO      2014132172 A1    9/2014

* cited by examiner

*Primary Examiner* — Tajash D Patel (57) ABSTRACT

The glove having chromogenic material is a medical glove that further comprises a chemical indicator. The chemical indicator is selected to indicate the presence of a specific chemical or chemical condition within a biological material that is being handled by the medical glove. The chemical indicator reacts to the specific chemical or chemical condition in a visible manner such that medical personnel handling the biological material is notified of the specific chemical or chemical condition. In the first potential embodiment of the disclosure, the chemical indicator that forms the coating indicates the pH of the biological material. In a second and third potential embodiment of the disclosure, the chemical indicator that forms the coating detects the presence of a biologically active chemical that is diagnostically relevant when found in the urine of a mammal.

16 Claims, 8 Drawing Sheets

GLOVE HAVING CHROMOGENIC MATERIAL

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of personal and domestic articles including protective garments, more specifically, a glove that further comprises a measurement instrument.

SUMMARY OF INVENTION

The glove having chromogenic material is a medical glove that further comprises a chemical indicator. The chemical indicator is selected to indicate the presence of a specific chemical or chemical condition within a biological material that is being handled by the medical glove. The chemical indicator reacts to the specific chemical or chemical condition in a visible manner such that medical personnel handling the biological material is notified of the specific chemical or chemical condition. In the first potential embodiment of the disclosure, the chemical indicator that forms the coating indicates the pH of the biological material. In a second and third potential embodiment of the disclosure, the chemical indicator that forms the coating detects the presence of a biologically active chemical that is diagnostically relevant when found in the urine of a mammal.

These together with additional objects, features and advantages of the glove having chromogenic material will be readily apparent to those of ordinary skill in the art upon reading the following detailed description of the presently preferred, but nonetheless illustrative, embodiments when taken in conjunction with the accompanying drawings.

In this respect, before explaining the current embodiments of the glove having chromogenic material in detail, it is to be understood that the glove having chromogenic material is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the glove having chromogenic material.

It is therefore important that the claims be regarded as including such equivalent construction insofar as they do not depart from the spirit and scope of the glove having chromogenic material. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
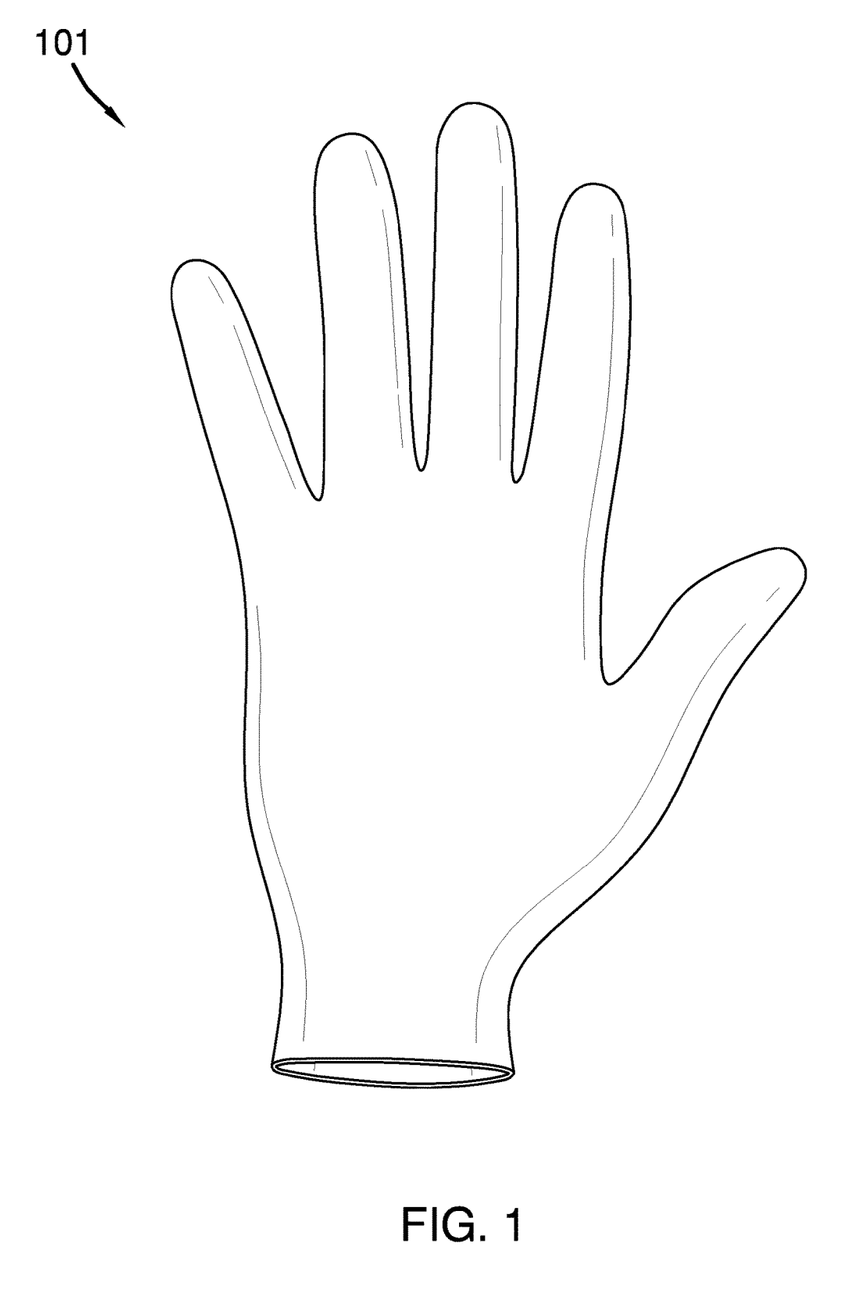
FIG. 1 is an inactive front view of an embodiment of the disclosure.
Figure 2:
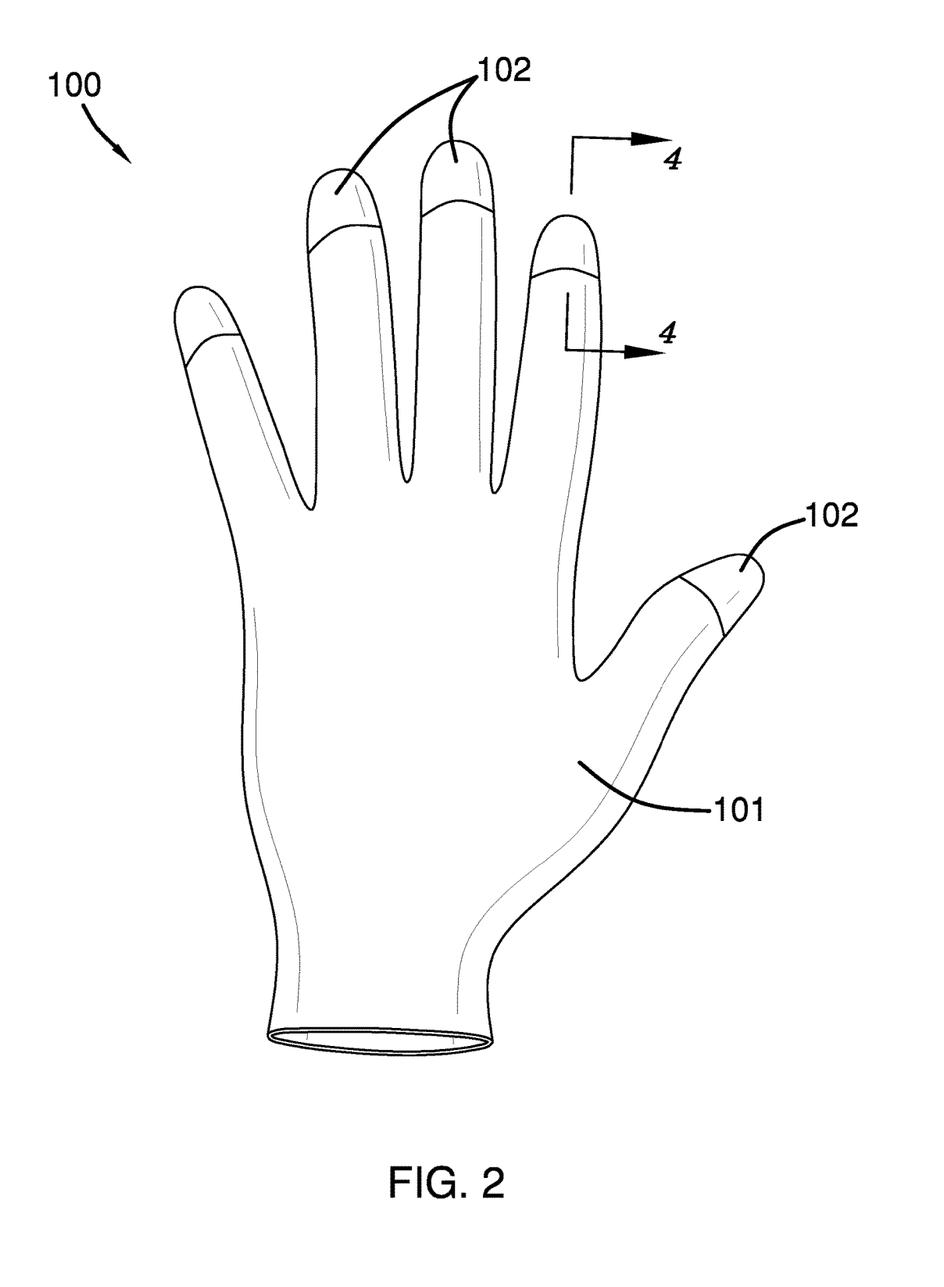
FIG. 2 is an active front view of an embodiment of the disclosure.
Figure 3:
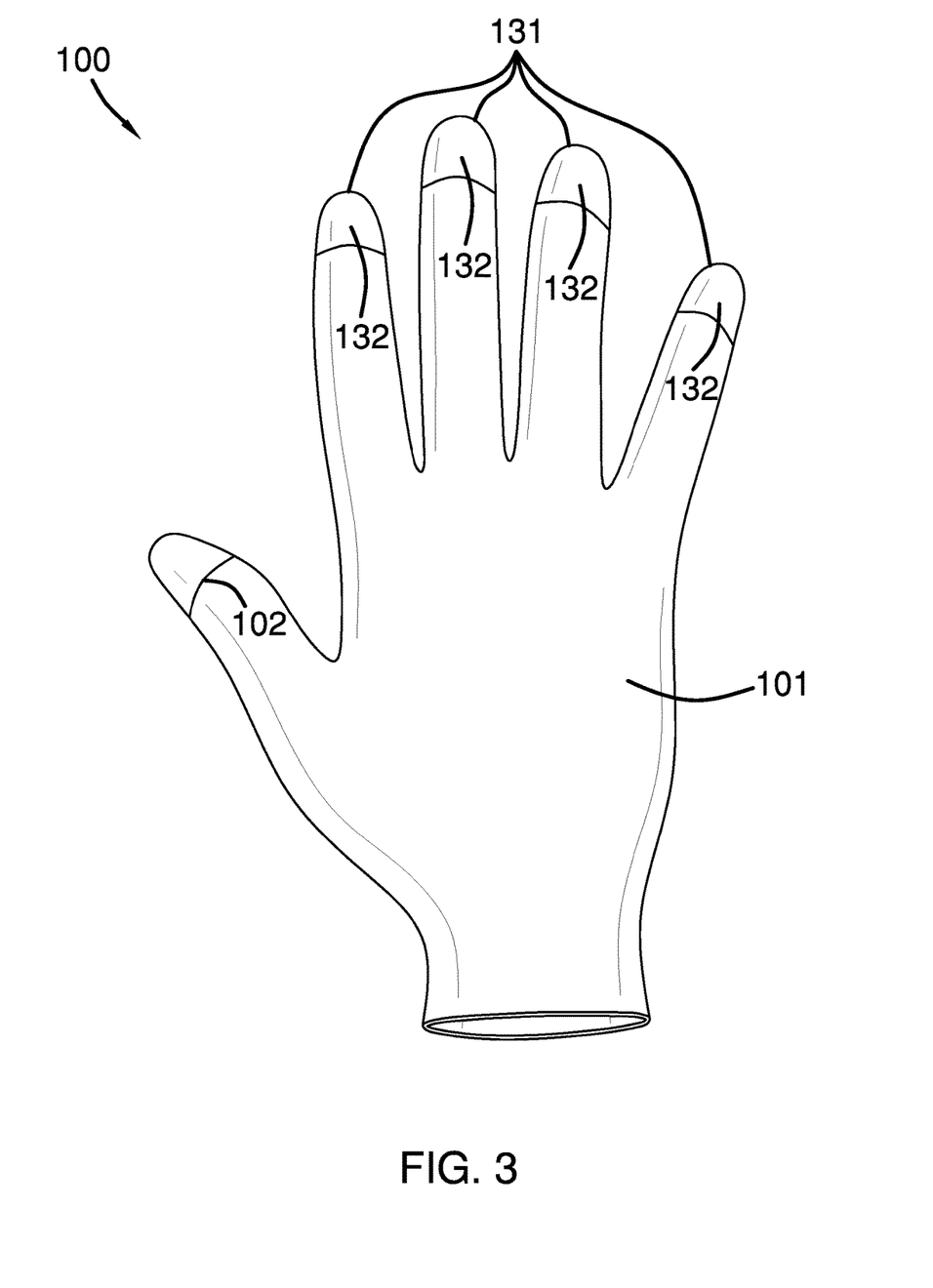
FIG. 3 is an active rear view of an embodiment of the disclosure.
Figure 4:
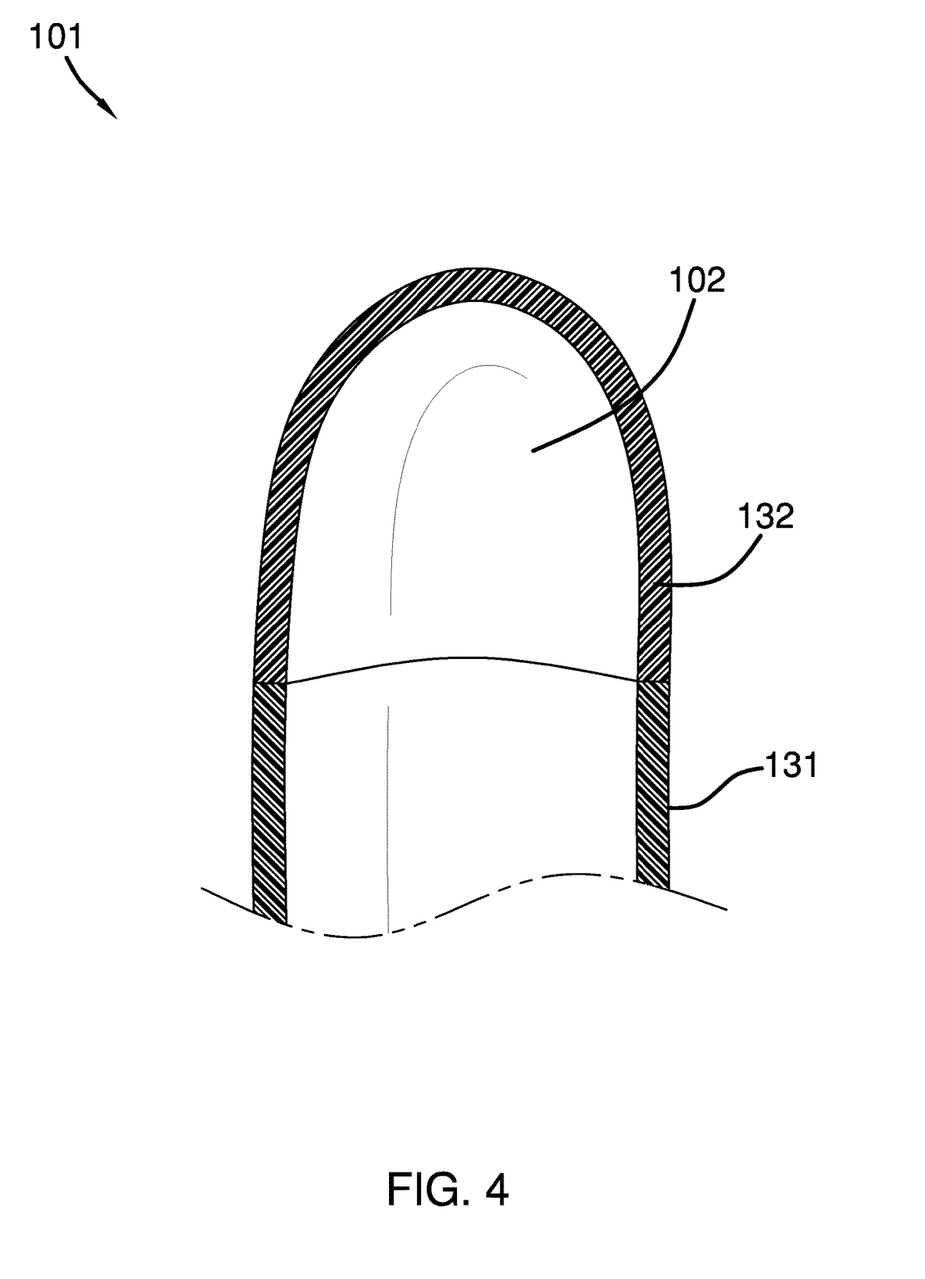
FIG. 4 is a cross-sectional view of an embodiment of the disclosure across 4-4 as shown in Figure Y.
Figure 5:
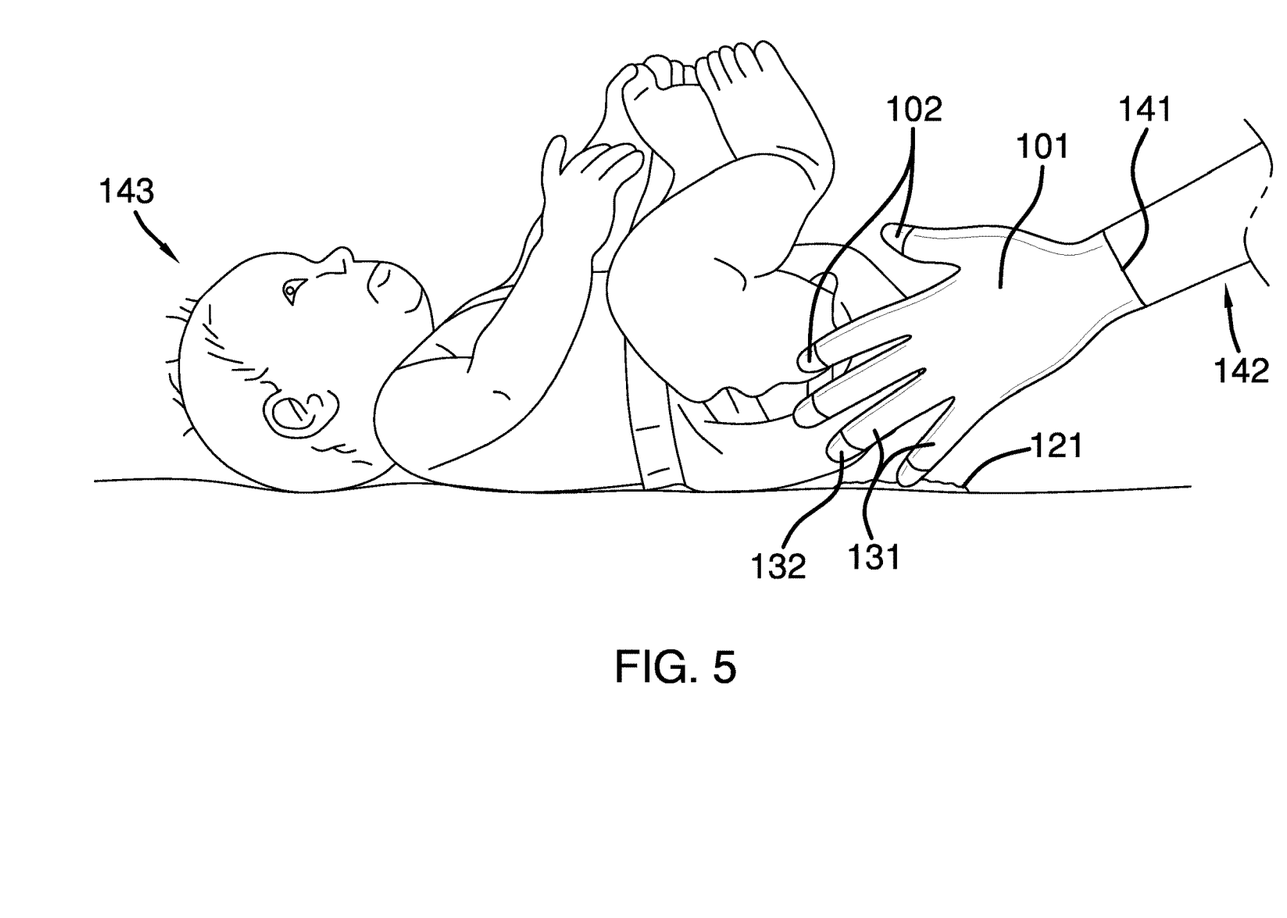
FIG. 5 is an in use view of an embodiment of the disclosure.
Figure 6:
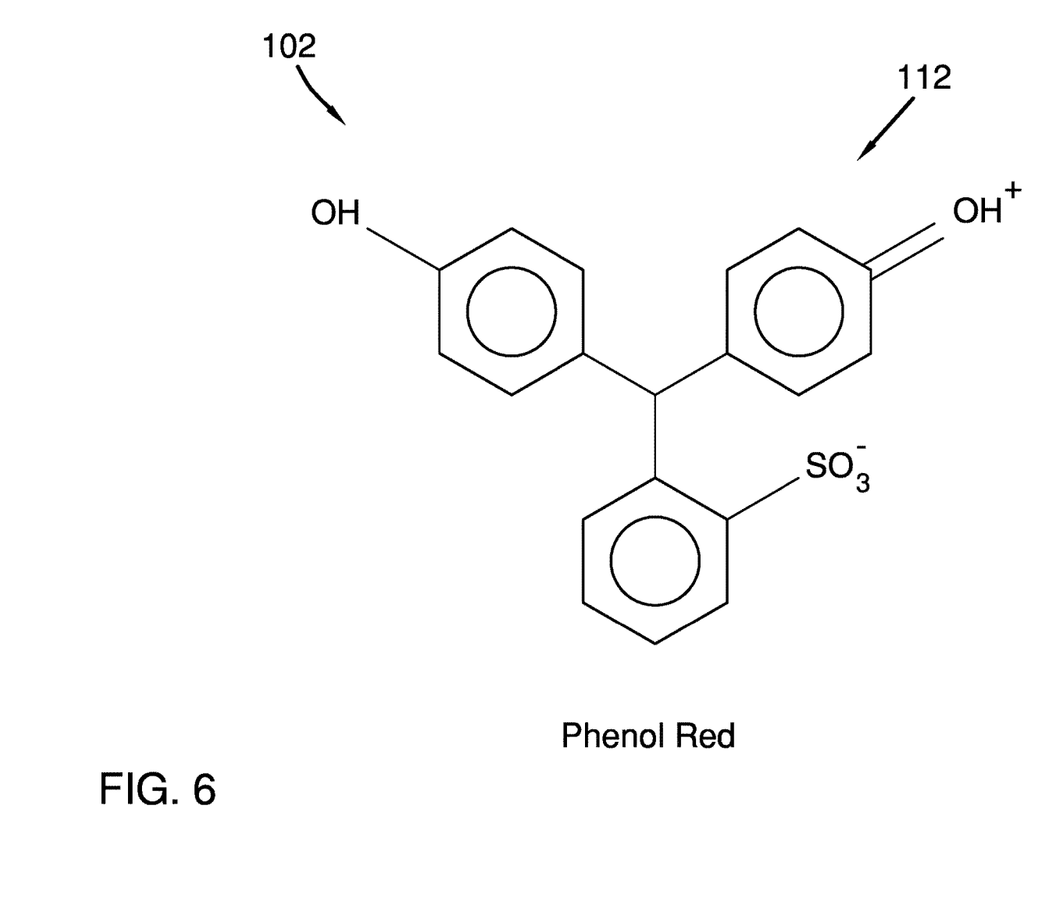
FIG. 6 is a detail view of an embodiment of the disclosure.
Figure 7:
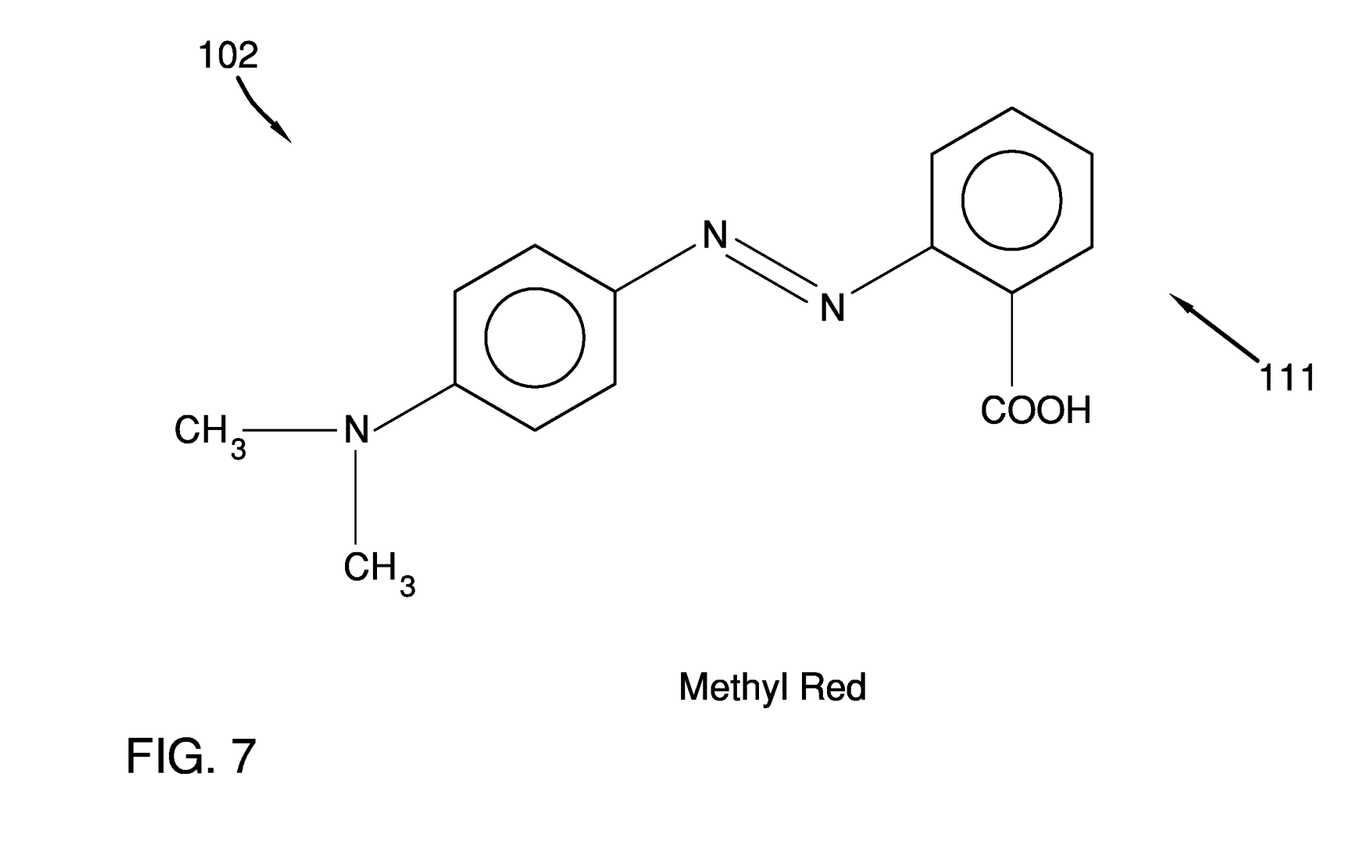
FIG. 7 is a detail view of an embodiment of the disclosure.
Figure 8:
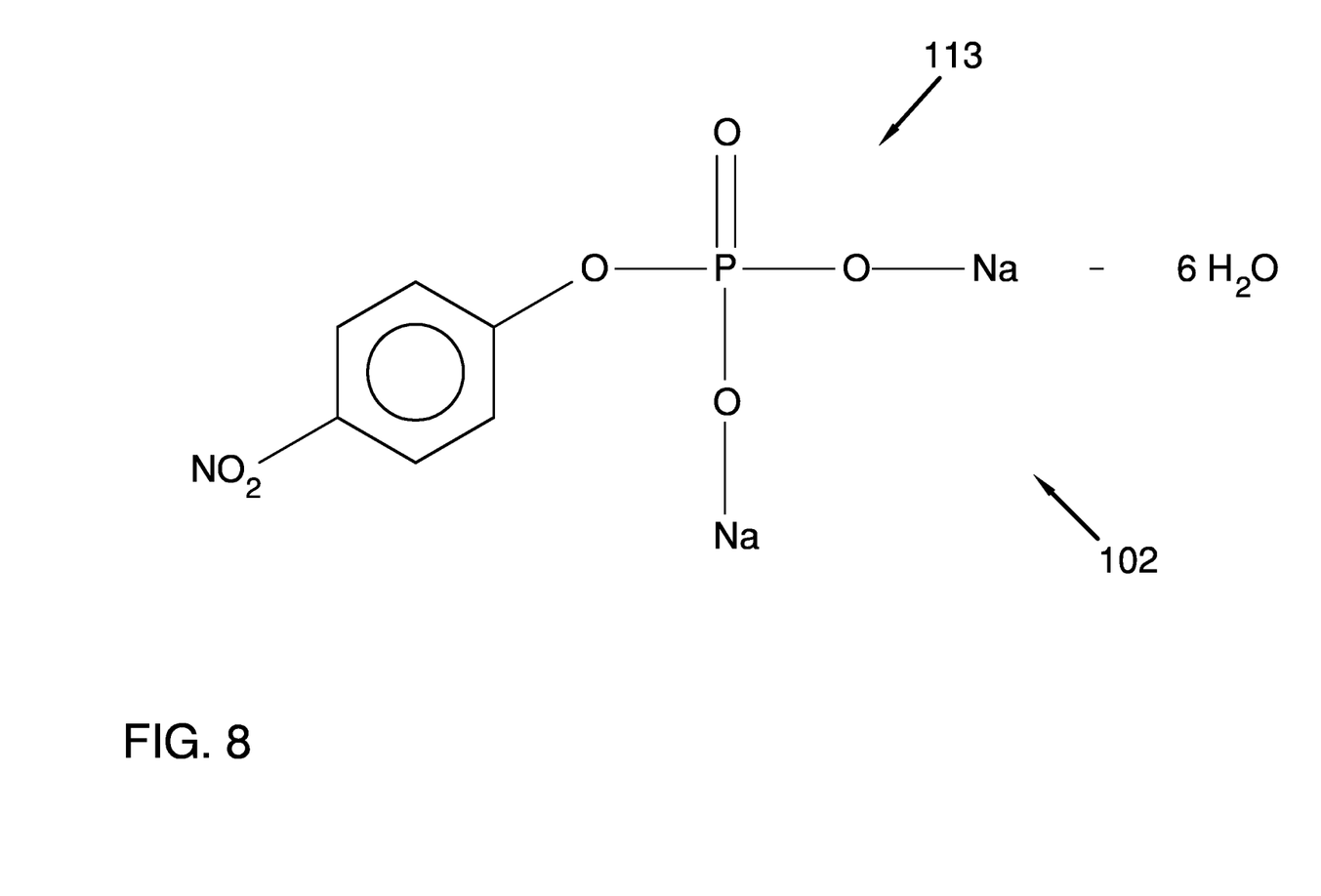
FIG. 8 is a detail view of an embodiment of the disclosure.

Detailed reference will now be made to one or more potential embodiments of the disclosure, which are illustrated in FIGS. 1 through 8.

The glove having chromogenic material 100 (hereinafter invention) is a medical glove 101 that further comprises a chemical indicator. The chemical indicator is a chemical substance that is selected to indicate the presence of a specific chemical or a specific chemical condition within a biological material 121 that is being handled by the medical glove 101. The chemical indicator reacts to the specific chemical or chemical condition in a visible manner such that the caregiver handling the biological material 121 is notified of the specific chemical or chemical condition. The invention 100 comprises a medical glove 101 and a coating 102. In the first potential embodiment of the disclosure, the chemical indicator that forms the coating 102 indicates the pH of the biological material 121. In a second and third potential embodiment of the disclosure, the chemical indicator that forms the coating 102 detects the presence of a biologically active chemical within the biological material 121 that is diagnostically relevant when found in the urine of a mammal.

The biological material 121 refers to a biological substance derived from a patient 143 that a caregiver 142 is required to handle as part of the responsibility of the caregiver 142. The experience is that when the indicating reaction is a hydrolyzing reaction, the biological material 121 is able to provide the necessary water when the invention 100 is used within 10 minutes of the generation of the biological material 121.

The medical glove 101 is further defined with a plurality of fingers 131. Each of the plurality of fingers 131 is further defined with a fingertip 132. The medical glove 101 is a protective garment that is worn on a hand 141 as a glove. The medical glove 101 forms a barrier between the hand 141 and the biological material 121. It is preferred that the medical glove 101 be white in color. Medical gloves are well known and documented in the medical arts.

The plurality of fingers 131 refers to an accommodation formed within the medical glove 101 to receive the fingers of the hand 141 of the caregiver 142. The fingertip 132 refers to the distal end of any finger selected from the plurality of fingers 131 of the medical glove 101. The hand 141 refers to the hand 141 of the caregiver 142. The caregiver 142 refers to a person who is responsible for handling biological material 121.

The coating 102 is a chemical substance that is applied to the exterior surface of the medical glove 101. The coating 102 is applied to the fingertip 132 of each of the plurality of fingers 131. The chemical substance that forms the coating 102 is used as an indicating substance. Specifically, the chemical substance that forms the coating 102 is selected to chemically react to a specifically identified chemical substance or a specifically identified chemical condition. The chemical substance that forms the coating 102 is further selected to react with the specific chemical substance or specific chemical condition by changing color in a visible manner.

The coating 102 is applied by dissolving the chemical substance that forms the coating 102 into a solvent to form a solution. The solution is then applied as a liquid coat on the exterior surface of each fingertip 132 of the medical glove 101. The solvent is then evaporated off of the medical glove 101 by air drying or oven drying. Depending on the application and on the solubility of the chemical substance that forms the coating 102, the preferred solvent is selected from the group consisting of water, ethanol, or a short chain fatty acid. Other potentially useful solvents include, but are not limited to, carbon disulfide and dimethyl sulfide.

As the medical glove 101 handles the biological material 121, the chemical substance that forms the coating 102 is brought into contact with the biological material 121. If the specified chemical or specified chemical condition exists within the biological material 121 handled by the medical glove 101, a chemical reaction occurs between the chemical substance that forms the coating 102 and the specific chemical or specific chemical condition. This reaction results in a visible change of color in the medical glove 101 thereby indicating to the caregiver 142 that the specified chemical or chemical condition exists within the biological material 121.

In the first potential embodiment of the disclosure, the coating 102 comprises a combination of methyl red 111 and a phenol red 112. The phenol red 112 is a well-known and documented chemical that is used to indicate pH levels between 6.4 and 8. The color of phenol red 112 ranges from red at pH 6.4 or below to yellow at pH 8 or above.

The methyl red 111 is a well-known and documented chemical that is used to indicate pH levels between 4.4 and 6.2. The color of methyl red 111 ranges from red at pH 4.4 or below to yellow at pH 6.2 or above. The combination of the methyl red 111 and the phenol red 112 result in a coating 102 that reacts to the pH level of the biological material 121. The colors of the first potential embodiment of the disclosure range from red at pH 4.4 through an orange in the pH 6.0 ranges to yellow at the pH 8.0 range.

In a second potential embodiment of the disclosure, the coating 102 comprises 4-nitrophenyl phosphate salt 113. The 4-nitrophenyl phosphate salt 113 is a well-known and documented enzyme substrate that is used to test for alkaline phosphatase. The presence of alkaline phosphatase within urine is a potentially relevant diagnostic condition of interest to a caregiver 142. When the 4-nitrophenyl phosphate salt 113 reacts with the alkaline phosphatase, the 4-nitrophenyl phosphate salt 113 will turn a visible yellow color In a third potential embodiment of the disclosure, the coating 102 comprises a chemical substance that detects creatinine. Creatinine is a common waste product of metabolism. The level of creatinine in the blood serum is considered an excellent indication of kidney function with a high level of creatinine being a bad thing. Conversely, a low level of creatinine in the urine, as measured by the lack of intensity of the color of the coupled enzyme reaction can be indicative of a problem within the patient 143.

The coating 102 comprises a commercially available chemical assay that is used for the identification of creatinine. The chemical assay is a proprietary but commercially available product that that detects creatinine through a coupled enzyme reaction. The commercially available assay is available in a form that is amenable to the coating 102 of a surface. When the commercially available assay reacts with the creatinine, the commercially available assay will visibly change color.

The following definitions were used in this disclosure:

4-nitrophenyl phosphate disodium hexahydrate: As used in this disclosure, 4-nitrophenyl phosphate disodium hexahydrate (CAS 333338-18-4) is a commercially available enzyme substrate that detects the presence of alkaline phosphatase (EC 3.1.3.1). The term 4-nitrophenyl phosphate salt is a synonym for 4-nitrophenyl phosphate disodium hexahydrate.

Alkaline Phosphatase: As used in this disclosure, alkaline phosphatase (EC 3.1.3.1) is an enzyme commonly found in biology. In certain situations, the presence of alkaline phosphatase in urine is of diagnostic significance EC: As used in this disclosure, EC used as an acronym for Enzyme Commission number. The Enzyme Commission number is a classification system that is commonly used to organize and identify an enzyme.

Enzyme Substrate: As used in this disclosure, an enzyme substrate is a chemical substance that is used to test for the presence of a previously specified enzyme. Generally, the chemical substance will contain a link that the previously specified enzyme will break creating two known by-products. If tests of the enzyme substrate indicates the presence of either of the two known by-products the assumption is that the enzyme is present in the tested sample.

Methyl Red: As used in this disclosure methyl red is a common trade term for the chemical 2-(4-methylaminophenylazo) benzoic acid (CAS 493-52-7). Within this disclosure, methyl red is used as a pH indicator. When exposed to an acidic liquid with a pH of between 4.4 and 6.2, the color of methyl red will range from red at 4.4 and below to yellow at 6.2 and above.

Phenol Red: As used in this disclosure, phenol red is a common trade term for the chemical phenolsulfonphthalein (CAS 143-74-8). Within this disclosure, phenol red is used as a pH indicator. When exposed to an acidic liquid with a pH of between 6.4 and 8.0, the color of phenol red will range from red at 6.4 and below to yellow at 8.0 and above.

With respect to the above description, it is to be realized that the optimum dimensional relationship for the various components of the invention described above and in FIGS. 1 through 8 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An instrumented glove comprising:
   a medical glove and a coating;
   wherein the coating is formed from a chemical indicator;
   wherein the coating is applied to the exterior of the medical glove;
   wherein the instrumented glove is adapted for use with a caregiver;
   wherein the instrumented glove is configured for use with a patient;
   wherein the caregiver is further defined with a hand;
   wherein the instrumented glove is configured for use in handling biological material;
   wherein the biological material is biological substance derived from the patient;
   wherein the medical glove is further defined with a plurality of fingers;
   wherein each of the plurality of fingers is further defined with a fingertip;
   wherein the chemical indicator is a chemical substance that indicates the presence of a chemical event;
   wherein the chemical event is selected from the group consisting of a specific chemical or a specific chemical condition;
   wherein the chemical event is contained within the biological material;
   wherein the chemical indicator reacts to the chemical event in a visible manner;
   wherein as the medical glove handles the biological material the coating is brought into contact with the biological material;
   wherein if the chemical event exists within the biological material handled by the medical glove a chemical reaction occurs between the coating and the chemical event;
   wherein this reaction results in a visible change of color in the medical glove;
   wherein the medical glove is a protective garment that is worn on a hand as a glove;
   wherein the medical glove forms a barrier between the hand of the caregiver and the biological material;
   wherein the plurality of fingers are an accommodation formed within the medical glove to receive the fingers of the hand of the caregiver;
   wherein the fingertip refers to the distal end of any finger selected from the plurality of fingers of the medical glove;
   wherein the coating is applied to the fingertip of one or more fingers selected from the plurality of fingers.

2. The instrumented glove according to claim 1
   wherein the coating is applied by dissolving the chemical indicator into a solvent.

3. The instrumented glove according to claim 2 wherein the solution is applied as a liquid coat on the exterior surface of each fingertip of the medical glove.

4. The instrumented glove according to claim 3 wherein the solvent is then evaporated off of the medical glove using a method selected from the group consisting of air drying or oven drying.

5. The instrumented glove according to claim 1 wherein the solvent is selected from the group consisting of water, ethanol, or a short chain fatty acid.

6. The instrumented glove according to claim 5
   wherein the coating comprises a combination of methyl red and a phenol red;
   wherein the chemical event is the pH of the biological material.

7. The instrumented glove according to claim 6
   wherein the coating is applied by dissolving the chemical indicator into a solvent;
   wherein the solution is applied as a liquid coat on the exterior surface of each fingertip of the medical glove;
   wherein the solvent is then evaporated off of the medical glove using a method selected from the group consisting of air drying or oven drying.

8. The instrumented glove according to claim 5
   wherein the coating comprises 4-nitrophenyl phosphate salt;
   wherein the chemical event is the presence of alkaline phosphatase within the biological material.

9. The instrumented glove according to claim 8
   wherein the coating is applied by dissolving the chemical indicator into a solvent;
   wherein the solution is applied as a liquid coat on the exterior surface of each fingertip of the medical glove;
   wherein the solvent is then evaporated off of the medical glove using a method selected from the group consisting of air drying or oven drying.

10. The instrumented glove according to claim 5
    wherein the coating comprises a chemical substance that detects creatinine;
    wherein the chemical event is the presence of creatinine within the biological material.

11. The instrumented glove according to claim 1 wherein solvent is selected from the group consisting of carbon disulfide and dimethyl sulfide.

12. The instrumented glove according to claim 11
    wherein the coating comprises a combination of methyl red and a phenol red;
    wherein the chemical event is the pH of the biological material.

13. The instrumented glove according to claim 12
    wherein the coating is applied by dissolving the chemical indicator into a solvent;
    wherein the solution is applied as a liquid coat on the exterior surface of each fingertip of the medical glove;
    wherein the solvent is then evaporated off of the medical glove using a method selected from the group consisting of air drying or oven drying.

14. The instrumented glove according to claim 11
    wherein the coating comprises 4-nitrophenyl phosphate salt;
    wherein the chemical event is the presence of alkaline phosphatase within the biological material.

15. The instrumented glove according to claim 14
wherein the coating is applied by dissolving the chemical indicator into a solvent;
wherein the solution is applied as a liquid coat on the exterior surface of each fingertip of the medical glove;
wherein the solvent is then evaporated off of the medical glove using a method selected from the group consisting of air drying or oven drying.

16. The instrumented glove according to claim 11
wherein the coating comprises a chemical substance that detects creatinine;
wherein the chemical event is the presence of creatinine within the biological material.

* * * * *